(12) United States Patent
Gama De Abreu et al.

(10) Patent No.: US 6,840,906 B2
(45) Date of Patent: Jan. 11, 2005

(54) ARRANGEMENT FOR THE DETERMINATION OF THE EFFECTIVE PULMONARY BLOOD FLOW

(75) Inventors: Marcelo Gama De Abreu, Dresden (DE); Detlev Michael Albrecht, Dresden (DE)

(73) Assignee: Technische Universitaet Dresden, Dresden (DE)

( * ) Notice: Subject to any disclaimer, the term of this patent is extended or adjusted under 35 U.S.C. 154(b) by 0 days.

(21) Appl. No.: 10/400,595

(22) Filed: Mar. 27, 2003

(65) Prior Publication Data

US 2004/0087867 A1 May 6, 2004

Related U.S. Application Data

(63) Continuation-in-part of application No. 10/097,064, filed on Mar. 13, 2002, now abandoned, which is a continuation of application No. 09/638,996, filed on Aug. 14, 2000, now Pat. No. 6,394,962, which is a continuation of application No. 09/269,458, filed as application No. PCT/DE97/02194 on Sep. 26, 1997, now Pat. No. 6,106,480.

(30) Foreign Application Priority Data

Sep. 28, 1996 (DE) .......................................... 196 40 152
Sep. 24, 1997 (DE) .......................................... 197 42 226

(51) Int. Cl.[7] .............................................. A61B 5/08
(52) U.S. Cl. ..................................... 600/532; 600/529
(58) Field of Search .................................. 600/529, 531, 600/532, 533, 537, 538; 128/204.18, 204.22, 204.23, 204.24, 203.22

(56) References Cited

U.S. PATENT DOCUMENTS

| | | | | |
|---|---|---|---|---|
| 6,059,732 A | * | 5/2000 | Orr et al. ..................... | 600/532 |
| 6,106,480 A | * | 8/2000 | Gama De Abreu et al. . | 600/529 |
| 6,200,271 B1 | * | 3/2001 | Kuck et al. .................. | 600/532 |
| 6,238,351 B1 | * | 5/2001 | Orr et al. ..................... | 600/532 |
| 6,394,962 B1 | * | 5/2002 | Gama De Abreu et al. . | 600/529 |

* cited by examiner

Primary Examiner—Robert L. Nasser
Assistant Examiner—Navin Natnithithadha
(74) Attorney, Agent, or Firm—Jordan and Hamburg LLP

(57) ABSTRACT

The invention relates to a device to determine effective pulmonary blood flow (PBF) by means of partial $CO_2$ rebreathing. The device is characterized in that it comprises an endotracheal tube whose conduit leading from the patient to the respirator is divided up into two lines between a controllabe three-way valve (4) and a Y-piece; one line forms a larger dead area (6) for $CO_2$ rebreathing whereby, in order to measure $CO_2$ elimination and end expiratory partial $CO_2$ pressure, a $CO_2$ sensor (3) and a respiration flow sensor (1) are provided on the endotracheal tube of the patient. The calculation of effective pulmonary blood flow is provided by a microprocessor/controller (7) which also controls the three-way valve (4) which provides the switching between both lines.

6 Claims, 2 Drawing Sheets

ARRANGEMENT FOR THE DETERMINATION OF THE EFFECTIVE PULMONARY BLOOD FLOW

REFERENCE TO RELATED APPLICATIONS

Figure 1:
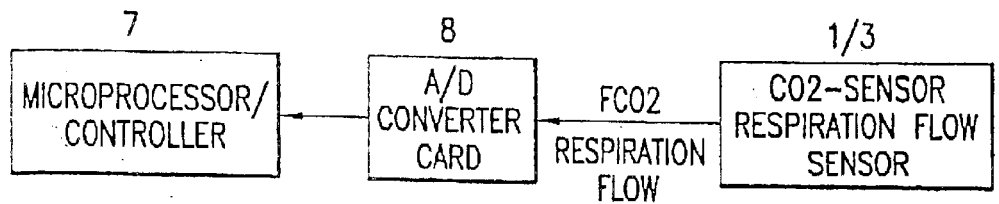

This is a continuation-in-part of Ser. No. 10/097,064, filed Mar. 13, 2002 now abandoned, which is a continuation of Ser. No. 09/638,996, filed Aug. 14, 2000, now U.S. Pat. No. 6,394,962, which is a continuation of Ser. No. 09/269,458, filed Apr. 23, 1999, now U.S. Pat. No. 6,106,480.

BACKGROUND OF THE INVENTION

The invention relates to an arrangement for the determination of the effective pulmonary blood flow.

From the paper Steinhart, C. M., Burch, K. D., Bruno, S., Parker, D. H.: Noninvasive determination of effective (nonshunted) pulmonary blood flow in normal and injured lungs, Crit. Care Med., 1989, Vol. 17, No. 4, pp. 349–353 the Multiple-Inert-Gas method with rebreathing of helium, acetylene and carbon monoxide in oxygen and nitrogen from a respiratory bag is known. A disadvantage of this measurement is the relatively great effort to prepare the gas mixtures for rebreathing, the demand for special measuring instruments that can measure the concentrations of gases in the breathed air or the breathing flow, respectively, and the necessity of a person to connect the respiratory bag to the patient and maintain it. For those reasons the measurement of the effective pulmonary blood flow can only be executed by specialists and is for research purposes in almost all cases.

Further, from the paper by Inman, M. D., Hughson, R. L., and Jones, N. L.: Comparison of cardiac output during exercise by single-breath and $CO_2$ rebreathing methods, J. Appl. Physiol., Vol. 58, pp. 1372–1377, 1985, the total $CO_2$ rebreathing method and the so-called single-breath method are known. Disadvantages of these methods are distinct increases of $CO_2$ pressure in the arterial blood, as the $CO_2$ elimination is interrupted, and the impeding of the respiration. Other disadvantages are those of the Multiple-Inert-Gas method, namely the preparation of gas mixtures for rebreathing having certain $CO_2$ concentrations, the demand for special measuring instruments that can measure the concentrations of gases in the breathed air or the breathing flow, respectively, and the necessity of a person to connect the respiratory bag to the patient and maintain it.

Another method known is a partial $CO_2$ rebreathing method (according to Gedeon, A., Forslund, L., Hedenstierna, G. and Romano, E.: a new method for noninvasive bedside determination of pulmonary blood flow, Med. & Biol. Eng. & Comp., 1980, Vol. 18, pp. 411–418) based on varying minute ventilation. Disadvantage of this method is the variation of the mean respiratory tract pressure and of the pressure at the end of expiration. Due to this variation of the respiratory tract pressure the pulmonary blood flow also varies and both the mechanical stability of the lungs and the gas exchange are impeded.

From the paper by Capek, J. M. and Roy, R. J.: Noninvasive measurement of cardiac output using partial $CO_2$ rebreathing; IEEE Transactions on Biomedical Engineering, 1988, Vol. 35, No. 9, pp. 653–661) the partial $CO_2$ rebreathing method with change of the dead space of the apparatus is known, which is performed using a mass spectrometer and special respiratory flow sensors at the endotracheal tube and can measure the total cardiac output. The change between two different dead spaces is performed by a PC-controlled electromagnetic valve. The partial expiration termination pressure and the $CO_2$ elimination are determined for the respiration by both dead spaces. The $CO_2$ partial pressure at the end of expiration is converted to the arterial $CO_2$ concentration and the total cardiac output can be calculated from the division of the $CO_2$ elimination difference by the arterial $CO_2$ concentration difference. A disadvantage of this method is the demand for apparatus for the measurement of the $CO_2$ concentration in the breathed air (mass spectrometer) and of the respiratory flow at the endotracheal tube (Fleisch pneumatocograph).

It is the objective of this invention to describe a clinically practicable arrangement for noninvasive determination of the effective pulmonary blood flow whereby the effective pulmonary blood flow is the cardiac output minus the intrapulmonary shunt proportion. Only that portion of the cardiac output is intended to be determined which is available for gas exchange. This arrangement requires only little apparatus, does not essentially influence the respiratory schedule, and is capable of being automated.

SUMMARY OF THE INVENTION

Figure 2:
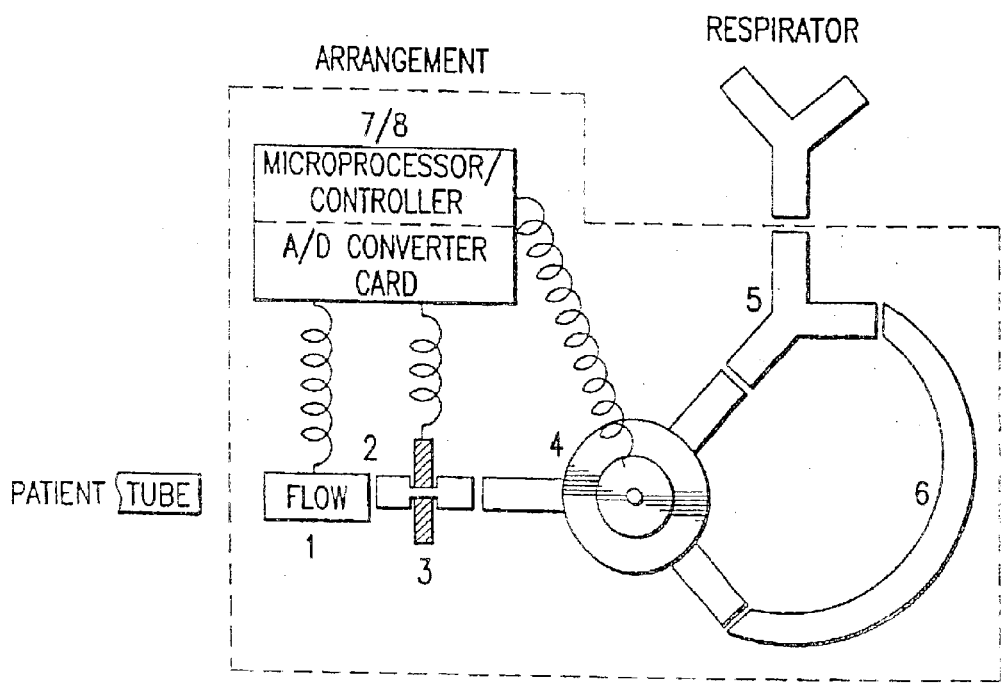

According to the invention, the problem is solved using features given by Claim 1. The dependant subclaims give other useful developments and embodiments. The selected parameters, above all, made it possible for the first time to determine the effective pulmonary blood flow during respiration, i.e. only that portion of the cardiac output that is available for gas exchange, In the arrangement according to the invention, which is controlled by a microprocessor or a controller, the signals of a main stream $CO_2$ sensor and a respiratory flow sensor are detected. The main stream $CO_2$ sensor is intended for measurement of the $CO_2$ concentration of the respiratory air, the respiratory flow sensor for measurement of the respiratory flow (FIG. 1). The respiratory flow sensor is located between the endotracheal tube and the $CO_2$ sensor. There is a controllable 3-way valve between the endotracheal tube and the Y-fitting of the respirator. This valve is switched by the microprocessor or the controller so that the patient is respirated through a short or a long branch (so-called dead space) (FIG. 2).

Measurements of the $CO_2$ elimination and expiration termination $CO_2$ partial pressure are first performed during respiration through the small dead space. This period lasts approx. 60 s, and is called non-rebreathing period. After this period during an inspiratory cycle the 3-way valve is switched so that the patient is respirated through the bigger dead space (long branch) and rebreathes a gas mixture that consists of his or her own expired air and fresh air from the respirator. Thus no separate $CO_2$ source for rebreathing is required. The time for switching the 3-way valve is derived from the absence of $CO_2$ in the inspiratory air. This causes no essential variation of the respiratory pressure. The subsequent period last approx. 30 s and is called rebreathing period. The $CO_2$ elimination and the expiration termination $CO_2$ partial pressure of this period are measured as mean values of each variable during a plateau that forms in the range of 15 to 30 s during this period (second half).

The arrangement according to the invention creates the possibility to set the respiratory schedule of the patient in the respirator such that the maximum pulmonary blood flow is achieved with the lowest mean and expiration termination respiratory tract pressure. This lowers the risk of the patient to suffer from a barotrauma, i.e. lung damage due to increased airway pressure is avoided and, simultaneously, the oxygen supply to the organs is optimised. This solution also raises the possibility to monitor the haemodynamics of the patient noninvasively and to record it automatedly. If simultaneous measurements of the cardiac output are taken, the found solution makes it possible to measure the percentage of the non-breathed cardiac output (so-called intrapulmonary shunt) without the inspiratory oxygen concentration being increased and blood samples being required.

BRIEF DESCRIPTIONS OF THE DRAWINGS

Figure 3:
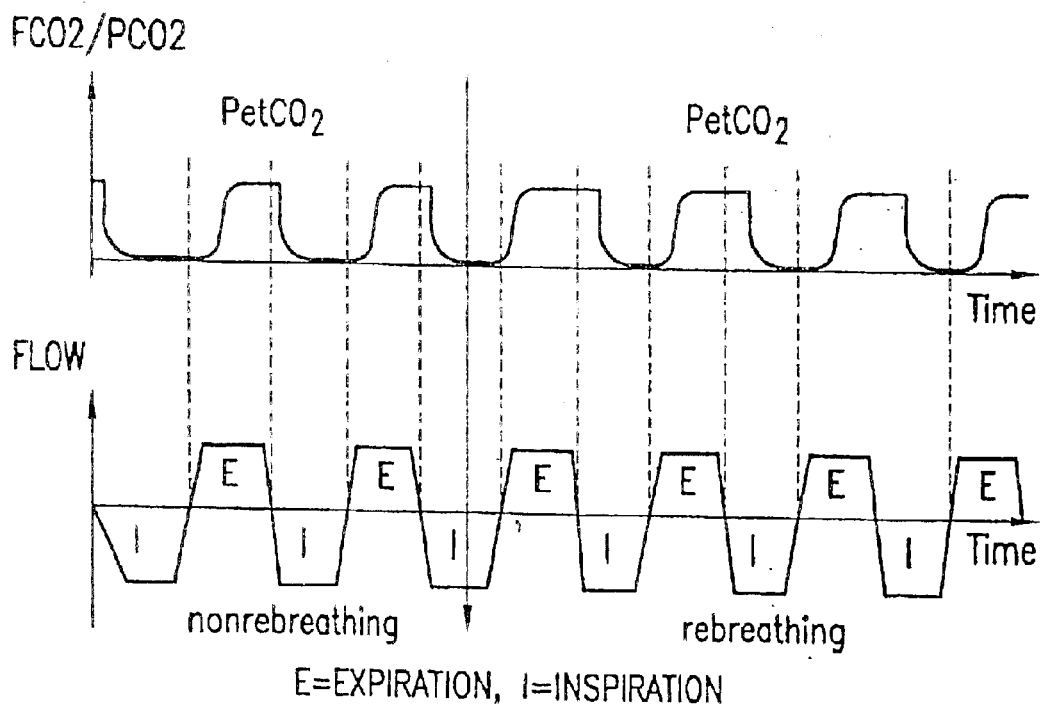
Figure 4:
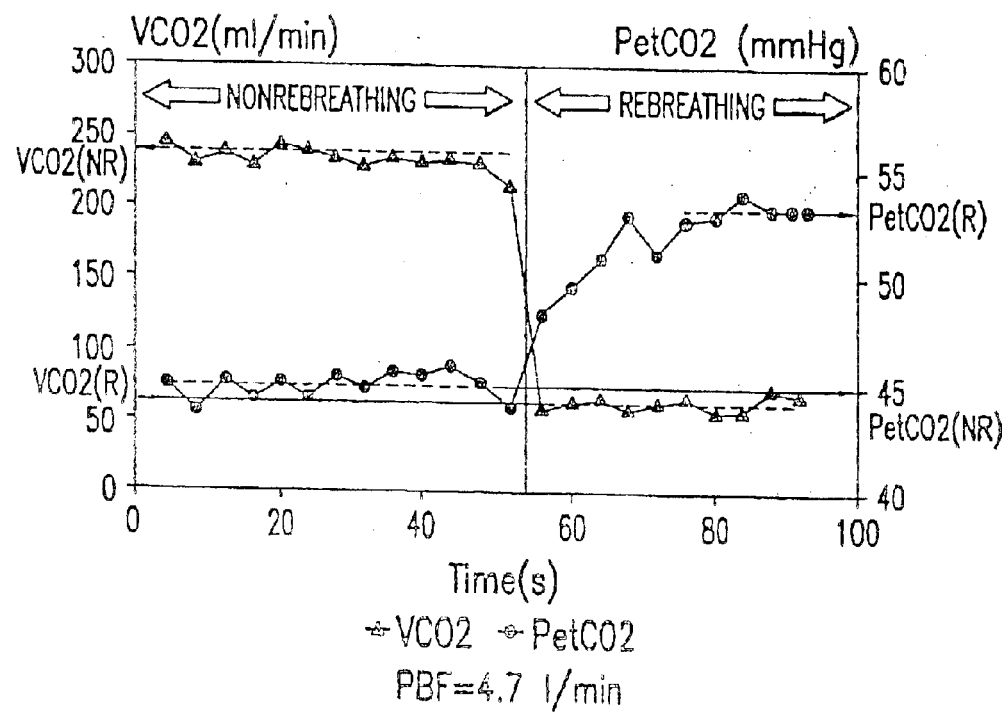

In the following, further details of the arrangement will be disclosed. By means of the accompanying drawing there are shown:

FIG. 1 an arrangement of a microprocessor or a controller for the measurement of the effective pulmonary blood flow FIG. 2 an arrangement according to the invention with a microprocessor/controller and respirator FIG. 3 an example of a $CO_2$ concentration and respiratory flow plot taken with the arrangement according to the invention FIG. 4 an example of an expiration termination $CO_2$ partial pressure and $CO_2$ elimination plot together with the calculated pulmonary blood flow.

DETAILED DESCRIPTION OF PREFERRED EMBODIMENTS

In FIG. 1, an arrangement of an microprocessor/controller for the measurement of the effective pulmonary blood flow that consists of four components is presented. The various components are connected with each other through cable and plug. According to FIG. 1 the system includes a microprocessor/controller 7 and an analog-digital-converter card 8 that registers and processes the $CO_2$ concentration and respiratory flow signals from the $CO_2$ sensor 3 or respiratory sensor 1, respectively.

In FIG. 2, a microprocessor- or controller-controlled arrangement for the measurement of the effective pulmonary blood flow is presented that consists of seven components, or less or more as desired. According to FIG. 2 the endotracheal tube of the patient is connected to one side of the respiratory flow sensor 1. To the other side of the respiratory flow sensor 1, a $CO_2$ cuvet 2 is connected. A $CO_2$ sensor 3 is inserted into the $CO_2$ cuvet 2. A switchable 3-way valve 4 is connected to the other side of the $CO_2$ cuvet 2. One of the outputs of the 3-way valve 4 is connected to a Y-fitting 5, the other output is connected to the dead space 6 for rebreathing. A respirator and the dead space 6 for rebreathing are also connected to the Y-fitting 5. The dead space 6 for rebreathing is about 200 ml, or less or more as desired, depending on the respiratory schedule of the patient. Alternatively, the dead space 6 may be adjustable in volume, typically from 50 to 15,000 ml. For example, the dead space 6 may be a highly flexible tube. A connection exists to the 3-way valve 4, through which the inner diaphragm of the valve 4 can be moved by pressure or flow. The microprocessor/controller 7 controls the 3-way valve 4, and senses and processes the $CO_2$ concentration and respiratory flow signals. The infrared $CO_2$ sensor 3 may be a mainstream or a sidestream sensor.

In FIG. 3, the curves of the $CO_2$ concentration in the respiratory air and of the respiratory flow during a measurement are presented. In the expiration period $CO_2$ is expired through the endotracheal tube. The $CO_2$ concentration ($FCO_2$) of the expired air, which corresponds with the $CO_2$ partial pressure ($PCO_2$) of the air, increases with the expired volume and reaches a maximum at the end of expiration. The $CO_2$ partial pressure at this time, the so-called expiration termination $CO_2$ partial pressure ($PetCO_2$), approximately corresponds with the $CO_2$ partial pressure in the ventilated pulmonary capillaries. During the nonrebreathing period $PetCO_2$ values are measured that only just differ. During the rebreathing period part of the expired $CO_2$ is rebreathed. Therefore the behaviour of the $CO_2$ partial pressure in the breathing air modifies and $PetCO_2$ increases.

In FIG. 4, the curves of the expiration termination $CO_2$ partial pressure corresponding with the maximum of the $CO_2$ concentration during expiration and of the $CO_2$ elimination per respiration during measurement using the arrangement according to the invention are given. The $CO_2$ elimination decreases during a partial $CO_2$ rebreathing and the expiration termination $CO_2$ partial pressure increases until a plateau has been reached, usually after approx. 15 s. The effective pulmonary blood flow is calculated from the four parameters given in FIG. 4, following the equation:

$$PBF = \frac{CO_2(NR) - VCO_2(R))}{f(f_1(PetCO_2(R)), f_2(PetCO_2(NR)), Hb) \times F_s}$$

$VCO_2(NR)$ is meant to be $CO_2$ elimination, in ml/min, during the nonbreathing period measured as the mean value of the $CO_2$ elimination of complete respirations within 60 s until immediately before the beginning of the rebreathing period. The nonrebreathing period can take 60 s or longer or shorter. The nonrebreathing period can also be represented by the period immediately after the rebreathing period, i.e., after the 3-way valve (4) has been in the rebreathing position. The $CO_2$ elimination can be measured taking the variations of $CO_2$ stores in the lungs into account and compensating for that variation when the respiratory pattern is not regular, as, for instance, during spontaneous breathing or modes of ventilation that allow the patient to trigger the mechanical ventilation or to have spontaneous breaths superposed to breaths originated form the mechanical ventilator. $PetCO_2(R)$ is the expiration termination $CO_2$ partial pressure, in mmHg, in the respiratory air during the nonrebreathing period measured as the mean value of expiration termination $CO_2$ partial pressures of complete respirations within 60 s until immediately before the beginning of the rebreathing period.

$PetCO_2(NR)$ is the expiration termination $CO_2$ partial pressure, in mmHg, in the respiratory air during the rebreathing period measured as the mean value of the expiration termination $CO_2$ partial pressures of complete respirations within 60 s until immediately before the beginning of the rebreathing period. The nonrebreathing period can take 60 s or longer or shorter. The partial pressures of complete respirations within 60 s until immediately before the beginning of the rebreathing period. The nonrebreathing period can take 60 s or longer or shorter. The nonrebreathing period can also be represented by the period immediately after the rebreathing period, i.e., after the 3-way valve (4) has been in the rebreathing position. The $PetCO_2(NR)$ can be estimated from a neural network or other filtering techniques if the values within the observation period are not constant.

$f_1$ is a function to better approximate the $PetCO_2$ to the end-capillary $CO_2$ partial pressure ($PcCO_2$) during the non-rebreathing period. This function can represent: a) the simple sum of the difference between the $CO_2$ partial pressure in arterial blood ($PaCO_2$), as determined invasively; b) the estimation of the difference between $PcCO_2$ and $PetCO_2$ according to gas exchange models that use alveolar deadspace and/or functional residual capacity (FRC) values that have been measured or estimated by normograms; c) the combination between invasive determined $PaCO_2$ and gas exchange models.

$VCO_2(R)$ is the $CO_2$ elimination, in ml/min, during the rebreathing period measured as the mean value of the $CO_2$ elimination of complete respirations within 15 to 30 s after the patient has begun to be respired through the big dead space 6, i.e. after switching of the 3-way valve 4 into the rebreathing position. The rebreathing period can be extended to 60 s or longer, but can also be shortened to 25 s or less. The $CO_2$ elimination can be alternatively measured taking the variations of $CO_2$ stores in the lungs into account and compensating for that variation when the respiratory pattern is not regular, as, for instance, during spontaneous breathing or modes of ventilation that allow the patient to trigger the mechanical ventilation or to have spontaneous breaths superposed to breaths originated from the mechanical ventilator. Alternatively, $VCO_2(R)$ can be measured form the first breath in the rebreathing period taking the FRC and the variation of breath-to-breath $PetCO_2$ or $PcCO_2$ differences into account in a gas exchange model. Also, curve fitting procedures can be applied to the breath-by-breath $VCO_2$ values measured or estimated in the rebreathing period in order to improve the estimation of $VCO_2(R)$.

$PetCO_2(R)$ is the expiration termination $CO_2$ partial pressure, in mmHg, in the respiratory air during the rebreathing period measured as the mean value of the expiration termination $CO_2$ partial pressures of complete respirations within 15 to 30 s after the patient has begun to be respired through the big dead space 6 (after switching of the 3-way valve 4 into the rebreathing position). The rebreathing period can be extended to 60 s or longer, but can also be shortened to 25 s or less. The time window of 15 to 30 s for taking the average value can be shortened or extended appropriately. Alternatively, $PetCO_2$ values can be entered into a curve fitting procedure to estimate $PetCO_2$ at equilibrium.

$f_2$ is a function to better approximate the $PetCO_2$ to the end-capillary $CO_2$ partial pressure ($PcCO_2$) during the rebreathing period. This function represents the estimation of the difference between $PcCO_2$ and $PetCO_2$ in the rebreathing period using gas exchange models that take the alveolar deadspace and/or the FRC measured or calculated by normograms into account. Such models may use or not the breath-by-breath $VCO_2$ into account. Estimated $PcCO_2$ values can be entered into a curve fitting procedure to estimate $PcCO_2$ at equilibrium.

Finally, the function $f(f_1(PetCO_2(R)), f_2(PetCO_2(NR)), Hb)$ is the standardized $CO_2$ dissociation curve in blood. By this function which has already been described in the literature (McHardy, G. J. R.: The relationship between the differences in pressure and concentration in arterial and venous blood, Cli. Sci., 1967 32, pp. 299–309), from the $PetCO_2(R)$ and $PetCO_2(NR)$ values and using also the haemoglobin concentration (Hb, g/dl), which has to be determined with a different device in a blood sample of the patient, the difference of the $CO_2$ concentrations ($\Delta CCO_2$, % by volume–ml/100 ml of blood) in the pulmonary capillary blood between the rebreathing and nonrebreathing periods is calculated using the following equation:

$$f(f_1(PetCO_2(R)), f_2(PetCO_2(NR)), Hb) = \Delta CCO_2 = 11.02 \times (PetCO_2(R)^{0.396} - PetCO_2(NR)^{0.396}) - 0.015 \times (15-Hb) \times (PetCO_2(R) - PetCO_2(NR))$$

Further, Fs is a scale factor for the representation of the effective pulmonary blood flow, in 1/min. Fs is defined to be 10.

From the calculation the effective pulmonary blood flow, PBF, in 1/min, is obtained.

What is claimed is:

1. Apparatus for the determination of the effective pulmonary blood flow by means of partial $CO_2$ rebreathing characterized in that an endotracheal tube;

a respirator;

the tube from the endotracheal tube of the patient to the respirator between a controllable 3-way valve (4) and a Y-fitting (5) is split into two branches, one branch forms a bigger dead space (6) for the $CO_2$ rebreathing whereby for measurement of the $CO_2$ elimination and expiration termination $CO_2$ partial pressure a $CO_2$ sensor (3) and a respiratory flow sensor (1) at the endotracheal tube of the patient and for calculation of the effective pulmonary blood flow a microprocessor/controller (7) is provided, the 3-way valve (4) switches between the two branches and controlled by the microprocessor/controller (7), the calculation of the effective pulmonary blood flow is performed using the equation:

$$PBF = \frac{(VCO_2(NR) - VCO_2(R))}{f(f_1(PetCO_2(R)), f_2(PetCO_2(NR)), Hb) \times F_s}$$

wherein $VCO_2(NR)$ is the $CO_2$ elimination (ml/min) during the nonrebreathing period measured as the mean value of the $CO_2$ elimination of complete respirations within 60 s until immediately before the beginning of the rebreathing period, the nonrebreathing period being about 60 s or longer or shorter or being the period immediately after the rebreathing period, the $CO_2$ elimination being measured taking variations of $CO_2$ stored in the lungs into account and compensating for the variations when the respiratory pattern is not regular, $PetCO_2(NR)$ is the expiration termination $CO_2$ partial pressure in mmHg in the respiratory air during the rebreathing period measured as the mean value of the expiration termination $CO_2$ partial pressures of complete respirations within 60 s until immediately before the beginning of the rebreathing period, $f_1$ is a function to better approximate the $PetCO_2$ to the end-capillary $CO_2$ partial pressure $PcCO_2$ during the nonrebreathing period, the function $f_1$ representing the simple sum of the difference between the $CO_2$ partial pressure in arterial blood $PaCO_2$ as determined invasively, the estimation of the difference between $PcCO_2$ and $PetCO_2$ according to gas exchange models that use alveolar deadspace and/or functional residual capacity values that have been measured or estimated by normograms or a combination of invasively determined $PaCO_2$ and gas exchange models, $VCO_2(R)$ is the $CO_2$ elimination in ml/min during the rebreathing period measured as the mean value of the $CO_2$ elimination of complete respirations within 15 to 30 s after the patient has begun to be respired through the big dead space (6) after switching the 3-way valve (4) into the rebreathing position, the rebreathing period being as long as 60 s or more and as short as 25 s or less, $CO_2$ elimination being alternatively measurable taking variations of $CO_2$ stored in the lungs into account and compensating for that variation when the respiratory pattern is not regular, $VCO_2(R)$ being measurable alternatively from the first breath in the rebreathing period talking the FRC and the variation of breath-to-breath $PetCO_2$ or $PcCO_2$ differences into account in a gas exchange model, and curve fitting procedures being applicable to the breath-by-breath $VCO_2$ values measured or estimated in the rebreathing period in order to improve the estimation of $VCO_2(R)$, $PetCO_2(R)$ is the expiration termination $CO_2$ partial pressure in mmHg in the respiratory air during the rebreathing period measured as the mean value of the expiration termination $CO_2$ partial pressures of complete respirations within 15 to 30 s after the patient has begun to be respired through the big dead space (6) after switching the 3-way valve (4) into the rebreathing position, a time window of 15 to 30 s for taking the mean value being subject to being shortened or extended, alternatively, $PetCO_2$ values being subject to a curve fitting procedure to estimate $PetCO_2$ at equilibrium, Fs is a scale factor for the representation of the effective pulmonary blood flow in 1/min with Fs=10, PBF is the effective pulmonary blood flow (1/min) whereby $f(f_1(PetCO_2(R)), f_2(PetCO_2(NR)), Hb)$ is the standardised $CO_2$ dissociation curve in blood and is calculated by inserting the measured values into the equation $$f(f_1(PetCO_2(R)), f_2(PetCO_2(NR)), Hb) = \Delta CCO_2 = 11.02 \times (PetCO_2(R)^{0.396} - PetCO_2(NR)^{0.396}) - 0.015 \times (15 - Hb) \times (PetCO_2(R) - PetCO_2(NR)).$$

2. Apparatus of claim 1 characterized in that the volume of the dead space (6) is adjustable.

3. Apparatus of claim 1 characterized in that the respiratory flow sensor (1) is inserted into the line at the endotracheal tube of the patient.

4. Apparatus of claim 1 characterized in that the $CO_2$ sensor (3) is an infrared sensor.

5. Apparatus of claim 4 characterized in that the infrared sensor is positioned in a $CO_2$ cuvet.

6. Apparatus of claim 4 characterized in that the infrared sensor is a mainstream or a sidestream sensor.

* * * * *